(12) United States Patent
Epstein et al.

(10) Patent No.: US 8,452,393 B1
(45) Date of Patent: May 28, 2013

(54) DEFIBRILLATION PADDLE STRUCTURE AND ITS ASSOCIATED METHOD OF USE

(76) Inventors: Stephen T. Epstein, Newtown, PA (US); André Martens, Linter (BE)

( * ) Notice: Subject to any disclaimer, the term of this patent is extended or adjusted under 35 U.S.C. 154(b) by 1286 days.

(21) Appl. No.: 11/267,428

(22) Filed: Nov. 7, 2005

(51) Int. Cl.
*A61N 1/00* (2006.01)

(52) U.S. Cl.
USPC .............................................. 607/5; 607/142

(58) Field of Classification Search
CPC ................................ A61N 1/3956; A61N 1/046
USPC ........................................................ 607/5, 142
See application file for complete search history.

(56) References Cited

U.S. PATENT DOCUMENTS

| | | | |
|---|---|---|---|
| 4,554,910 A * | 11/1985 | Lally ................................ | 601/41 |
| 4,681,112 A * | 7/1987 | Jones et al. ......................... | 607/5 |
| 4,705,044 A * | 11/1987 | Deluhery et al. ............. | 607/142 |
| 4,852,585 A * | 8/1989 | Heath ............................ | 600/397 |
| 5,645,522 A * | 7/1997 | Lurie et al. ....................... | 601/43 |
| 6,097,987 A * | 8/2000 | Milani ........................... | 607/142 |
| 6,360,125 B1 * | 3/2002 | Weil et al. .......................... | 607/5 |
| 6,721,597 B1 * | 4/2004 | Bardy et al. ....................... | 607/4 |
| 6,950,705 B2 * | 9/2005 | Bardy et al. ..................... | 607/36 |
| 6,961,611 B2 * | 11/2005 | Dupelle ............................. | 607/5 |
| 6,969,259 B2 * | 11/2005 | Pastrick et al. ................ | 434/265 |
| 7,016,727 B2 * | 3/2006 | Powers et al. ..................... | 607/5 |
| 7,245,974 B2 * | 7/2007 | Dupelle et al. ................. | 607/142 |
| 7,274,962 B2 * | 9/2007 | Bardy et al. ....................... | 607/5 |
| 2002/0042629 A1 * | 4/2002 | Bardy et al. ....................... | 607/5 |
| 2002/0062144 A1 * | 5/2002 | Zadini et al. ................... | 607/129 |
| 2002/0103510 A1 * | 8/2002 | Bardy et al. ....................... | 607/5 |
| 2002/0107548 A1 * | 8/2002 | Bardy et al. ....................... | 607/5 |
| 2003/0045905 A1 * | 3/2003 | Daynes et al. ..................... | 607/5 |
| 2003/0078470 A1 * | 4/2003 | Borst et al. ....................... | 600/37 |
| 2003/0191501 A1 * | 10/2003 | Miller et al. ...................... | 607/5 |
| 2004/0088035 A1 * | 5/2004 | W. Guenst et al. ............ | 607/131 |
| 2004/0162588 A1 * | 8/2004 | Watanabe et al. ................. | 607/5 |
| 2004/0172071 A1 * | 9/2004 | Bardy et al. ....................... | 607/5 |
| 2004/0186545 A1 * | 9/2004 | Rosero et al. ................. | 607/119 |
| 2004/0199236 A1 * | 10/2004 | Laske et al. ................... | 607/129 |
| 2004/0210259 A1 * | 10/2004 | Rock et al. ........................ | 607/5 |
| 2004/0230231 A1 * | 11/2004 | Thacker et al. ................... | 607/5 |
| 2005/0119705 A9 * | 6/2005 | Bardy et al. ....................... | 607/5 |
| 2005/0192639 A1 * | 9/2005 | Bardy et al. ....................... | 607/5 |
| 2005/0240232 A9 * | 10/2005 | Bardy et al. ....................... | 607/5 |
| 2006/0004416 A1 * | 1/2006 | Bardy et al. ....................... | 607/5 |
| 2006/0025826 A1 * | 2/2006 | Erlinger et al. ................... | 607/5 |
| 2006/0155337 A1 * | 7/2006 | Bardy et al. ....................... | 607/5 |
| 2006/0259081 A1 * | 11/2006 | Vaisnys et al. .................... | 607/5 |
| 2007/0233197 A1 * | 10/2007 | Jung et al. ......................... | 607/5 |
| 2007/0299473 A1 * | 12/2007 | Matos .............................. | 607/5 |
| 2008/0033495 A1 * | 2/2008 | Kumar .............................. | 607/5 |

\* cited by examiner

FOREIGN PATENT DOCUMENTS

EP             353341 A1 *    2/1990

*Primary Examiner* — Nicole F Lavert
(74) *Attorney, Agent, or Firm* — LaMorte & Associates P.C.

(57) ABSTRACT

A defibrillation system that utilizes a unique defibrillator paddle assembly. The defibrillator paddle assembly has a handle and a paddle head. The paddle head contains the conductive surface that is used to contact the muscle tissue of the heart during a defibrillation attempt. The paddle head is connected to the handle by a flexible connection. The flexible connection enables the relative orientation between the handle and the paddle head to be selectively adjusted. Accordingly, a physician can selectively change the orientation of the paddle head in relation to the handle in order to more effectively utilize the paddle assembly during a specific circumstance. The flexible connection between the handle and the paddle head can be adjusted either by manual bending or by utilizing adjustment controls that are present on the handle of the paddle assembly.

8 Claims, 4 Drawing Sheets

DEFIBRILLATION PADDLE STRUCTURE AND ITS ASSOCIATED METHOD OF USE

BACKGROUND OF THE INVENTION

1. Field of the Invention

In general, the present invention relates to defibrillation paddles. More particularly, the present invention relates to defibrillation paddles that are used internally within the body and directly contact the tissue of the heart.

2. Prior Art Description

It is known that a heart muscle that has stopped or is beating erratically can sometimes be caused to beat normally by passing an electric charge to the heart. The science of where, when and how to apply an electrical charge to the heart has been evolving for many years.

Defibrillators are machines that are specifically designed to pass an electrical charge into a patient's heart. In the field of defibrillators, there are non-intrusive defibrillators and intrusive defibrillators. Non-intrusive defibrillators have electrodes that attach to the skin of a patient. The non-intrusive defibrillators pass an electric charge through the body from one external point to another. Such non-intrusive defibrillators are used by rescue workers, paramedics and the like to revive a person whose heart may have stopped.

Since non-intrusive defibrillators pass electricity through the body, hoping to effect the heart, large electrical charges are used. These charges often cause the skin of the patient to burn at the areas where the defibrillator is attached to the body and where electricity passes into and out of the patient's body.

Intrusive defibrillators are used by physicians primarily in the operating room of hospitals. During many surgical procedures, a patient's heart may be temporarily stopped. In such situations, the patient's blood flow is transferred to an external pump. Once the surgical procedure is complete, a defibrillator is commonly used to restart the heart. When the heart muscle itself is exposed, the paddle terminals of the defibrillator are touched directly to the heart muscle. A small jolt of electricity is then passed through the tissue of the heart muscle to restart the heart's beat. Since the electricity is being applied directly to the heart muscle, smaller charges of electricity are used. However, even these smaller charges of electricity can result in some heart muscle tissue becoming burned in the areas of contact with the defibrillator's paddles.

One way to reduce the potential of damage to the heart muscle is to decrease the surface area of the heart that is physically contacted during a defibrillation attempt. In the prior art, defibrillator systems have been made that use only one paddle. In such systems, a patient is laid upon a conductive pad. A single paddle is provided. Both the single paddle and the conductive pad are connected to the defibrillator. The single paddle is then touched to the tissue of the heart. Electricity passes through the heart, through the back of the body and to the conductive pad. Since only one paddle is used, the area of the heart that directly contacts the paddle is reduced in half. Such prior art defibrillation systems are exemplified by Japanese Reference No JP2001121885, entitled Defibrillating Electrode And Defibrillation System.

A key to avoiding tissue damage made by a defibrillator paddle is to have uniform contact between the paddle and the tissue of the heart muscle. With prior art defibrillation systems, the paddle of the defibrillator is a fixed structure. That is, the contact surface of the defibrillator is at a fixed orientation with respect to the handle that is held by the physician.

Depending upon the reactions of the heart muscle, a doctor may decide to shock the heart at a specific spot. That location may be on the top of the heart or along one of the sides of the heart. However, it is often difficult to maneuver the defibrillator paddle to that portion of the heart while still maintaining a flush contact between the defibrillator paddle and the tissue of the heart. If there is not a flush contact, the odds greatly increase that the defibrillator paddle may cause an electrical burn upon the heart. Furthermore, without a flush contact, the defibrillator may fail to effect the heart muscle in the desired manner.

A need therefore exists for an improved defibrillator paddle design, wherein the orientation between the contact surface of the paddle and the handle of the paddle can be selectively adjusted. In this manner, the paddle can be oriented to the needs of the doctor, thereby making the defibrillator paddle less dangerous and more effective. This need is met by the present invention as described and claimed below.

SUMMARY OF THE INVENTION

The present invention is a defibrillation system that utilizes a unique defibrillator paddle assembly. The defibrillator paddle assembly has a handle and a paddle head. The paddle head contains the conductive surface that is used to contact the muscle tissue of the heart during a defibrillation attempt. The paddle head is connected to the handle by a flexible connection. The flexible connection enables the relative orientation between the handle and the paddle head to be selectively adjusted. Accordingly, a physician can selectively change the orientation of the paddle head in relation to the handle in order to more effectively utilize the paddle assembly during a specific circumstance.

The flexible connection between the handle and the paddle head can be adjusted either by manual bending or by utilizing adjustment controls that are present on the handle of the paddle assembly.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

Figure 1:
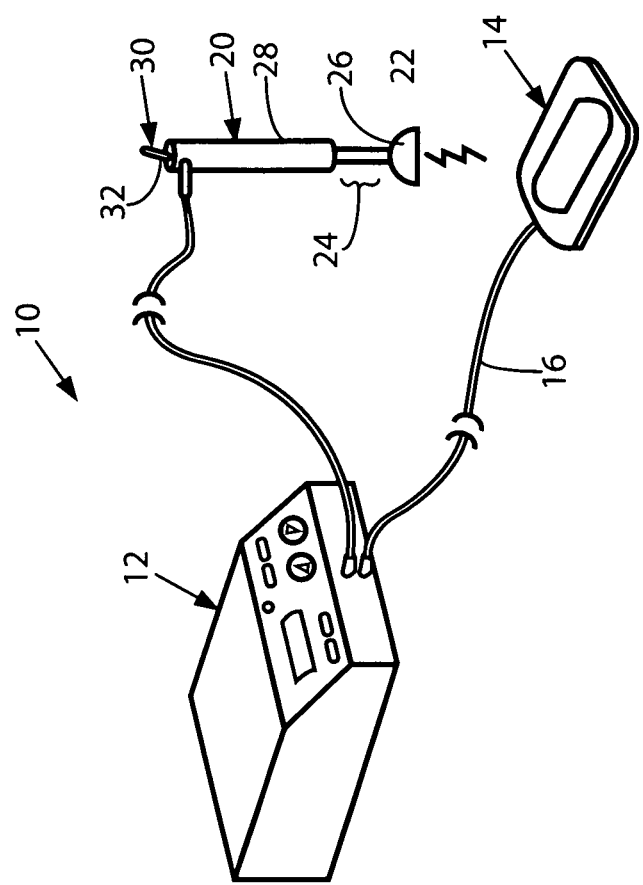
FIG. 1 is a perspective view of an exemplary embodiment of a defibrillation system.

Referring to FIG. 1, there is shown an exemplary embodiment of a defibrillation system 10 in accordance with the present invention. The defibrillation system 10 consists of a control unit 12 that controls the electrical charge that will be passed through the heart muscle. The control unit 12 has adjustable controls and safeguards typical in the industry. There are several defibrillator systems that are commercially available, the control unit of most any prior art defibrillator system can be adapted for use as part of the present invention defibrillation system.

A conductive pad 14 is provided. The conductive pad 14 is connected to the control unit 12 by a flexible terminal wire 16.

A paddle assembly 20 is also attached to the control unit 12 by a second flexible terminal wire 16. The paddle assembly 20 has a conductive contact surface 22. The control unit 12 creates an electrical bias between the conductive contact surface 22 of the paddle assembly 20 and the conductive pad 14. Accordingly, when both the contact pad 14 and the conductive contact surface 22 of the paddle assembly 20 are touched to a patient, electricity can flow through the patient between these surfaces.

The conductive contact surface 22 is supported by the paddle head 26. The paddle head 26 is set upon a flexible neck 24. The flexible neck 24 attaches the paddle head 26 to a handle 28. The physician using the paddle assembly 20 holds the paddle assembly 20 by grasping the handle 28.

An adjustment control 30 is provided on the handle 28. In the shown embodiment, the adjustment control 30 consists of an adjustment lever 32 that extends out the back of the handle 28. In this position, the adjustment lever 32 can be manipulated by a physician's thumb as the physician grasps the handle 28.

The adjustment control 30 is used to alter the orientation of the paddle head 26 and the conductive contact surface 22 in relation to the handle 28. In the shown embodiment, the conductive contact surface 22 of the paddle head 26 is held in a plane that is generally perpendicular to the longitudinal axis of the handle 28. However, by utilizing the adjustment control 30, the paddle head 26 can be selectively inclined. In this manner, a physician using the paddle assembly 20 can selectively change the orientation of the paddle head 26 and the conductive contact surface 22 so that the conductive contact surface 22 abuts flush against the heart muscle when in use.

Figure 2:
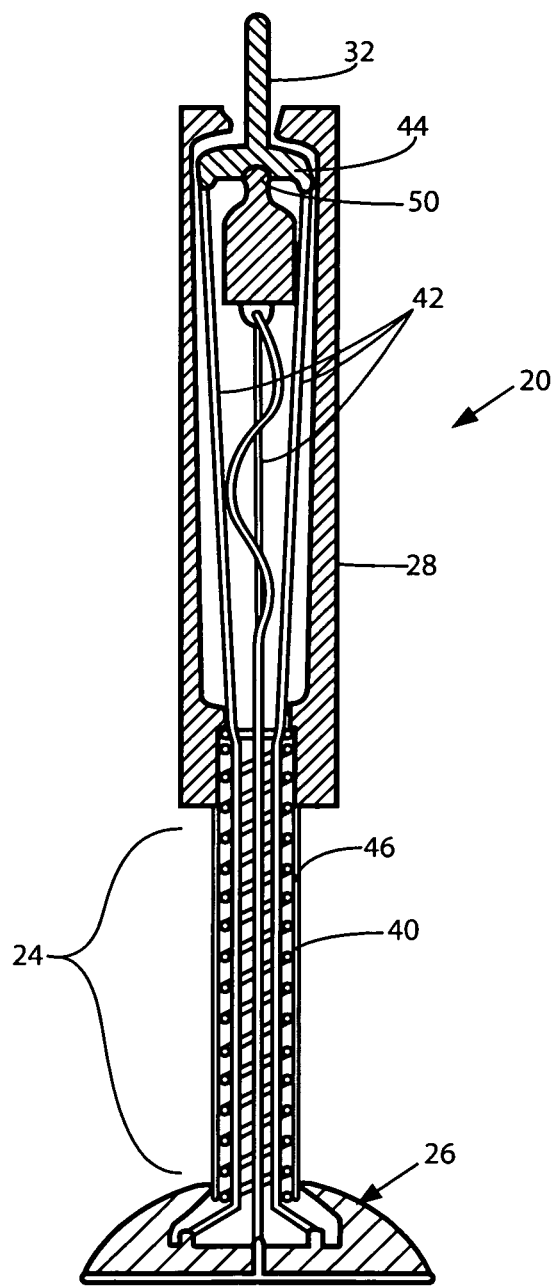
FIG. 2 is a cross-sectional view of a first exemplary embodiment of a paddle assembly, shown in a straight orientation.

Referring to FIG. 2, it can be seen that a spring 40 is present in the flexible neck 24 of the paddle assembly 20. The spring 40 has one end that attaches to the paddle head 26 and an opposite end that attaches to the handle 28. The spring 40, however, is partially compressed. Accordingly, the spring 40 acts to bias the paddle head 26 away from the handle 28.

The partial compression of the spring 40 is maintained by a plurality of guide wires 42. The guide wires 42 are symmetrically disposed around the inside periphery of the spring 40. Each guide wire 42 has one end that attaches to the paddle head 26. The opposite end of each guide wire 42 attaches to a wobble plate 44 at the bottom of the handle 28. The various guide wires 42 are all held taut by the bias action of the spring 40. The spring 40 also acts as a conduit for the guide wires 42. The guide wires 42 and spring 40 are surrounded by a flexible protective cover 46 in the area of the neck 24 in order to prevent these elements from directly contacting tissue during use of the paddle assembly 20. The terminal wire 48 that provides electricity to the conductive contact surface 22 extends through the handle 28 and through the center of the spring 40 in the flexible neck 24.

The wobble plate 44 is supported by a ball joint 50 at its center. The wobble plate 44 can therefore wobble about the central ball joint 50. The adjustment lever 32 extends away from the wobble plate 44 directly opposite the ball joint 50. Accordingly, it will be understood that by moving the adjustment lever 32 in a particular selected direction, the wobble plate 44 can also be caused to tip toward that selected direction.

Figure 3:
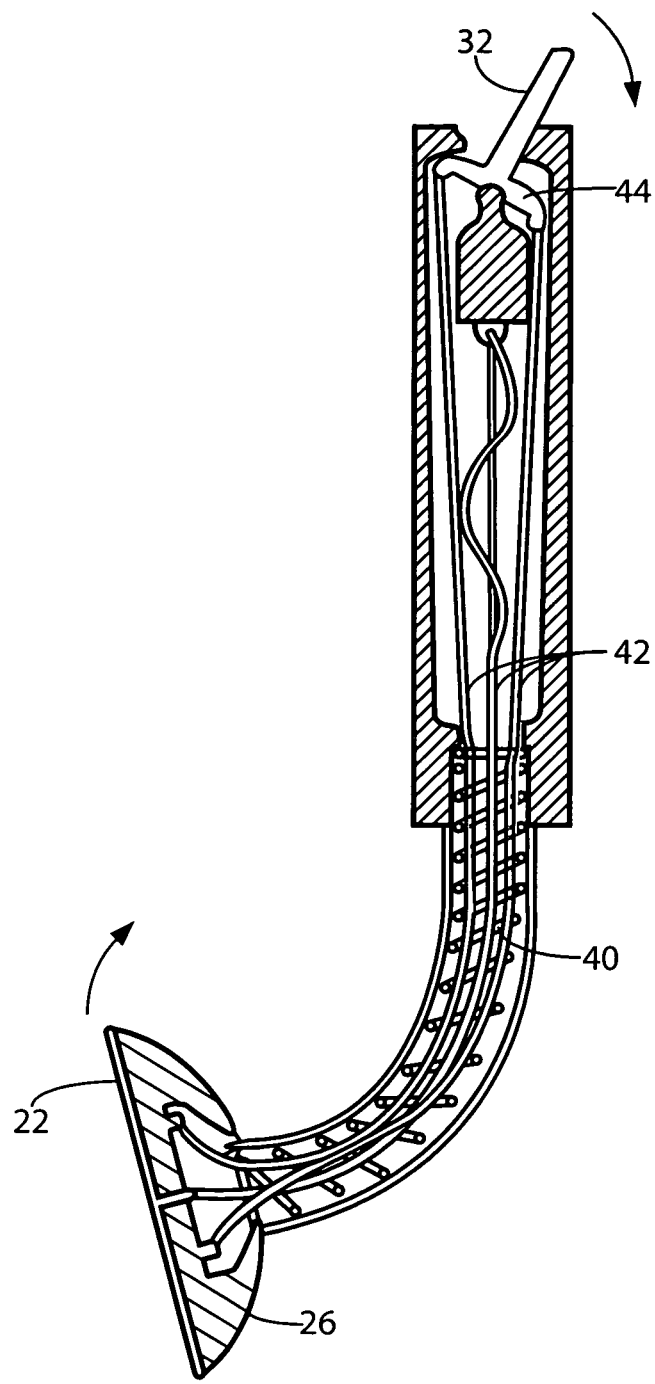
FIG. 3 is a cross-sectional view of the first exemplary embodiment of a paddle assembly, shown in a bent orientation.

Referring to FIG. 3, it can be seen that when the adjustment lever 32 is moved in a particular direction by a physician, the wobble plate 44 tilts toward that direction. When the wobble plate 44 tilts, the tension in the guide wires 42 at the high side of the wobble plate 44 slacken, while the guide wires 42 attached to the low side of the wobble plate 44 tighten. As the tension in the various guide 42 wires change, the orientation of the paddle head 26 changes. Due to the precompression of the spring 40, as the guide wires 42 on one side of the spring 40 slacken, the spring 40 will expand along that side. Similarly, as the guide wires 42 become more taut on one side of the spring 40, the spring 40 will compress farther along that side. The result is that the spring 40 will curve away from the slackening guide wires 42 and curve toward the tightening guide wires 42. Preferably, the curvature created in the spring 40 is enough to cause the spring 40 to change orientation by at least ninety degrees. It will be understood that since the adjustment lever 32 can be tilted in any desired direction, the wobble plate 44 can also be tilted in any desired direction. Since the movement of the wobble plate 44 creates a corresponding movement in the paddle head 26, the paddle head 26 can be selectively inclined in any selected direction.

By providing an adjustment mechanism that selectively changes the orientation of the paddle head 26 relative to the paddle handle, a physician can selectively control the orientation of the paddle head 26. The physician can therefore orient the conductive contact surface 22 to lay flush against the heart muscle, regardless of where on the heart muscle the physician decides to touch. This allows the defibrillator paddle to be more effective and present less danger than paddles with a fixed configuration.

Figure 4:
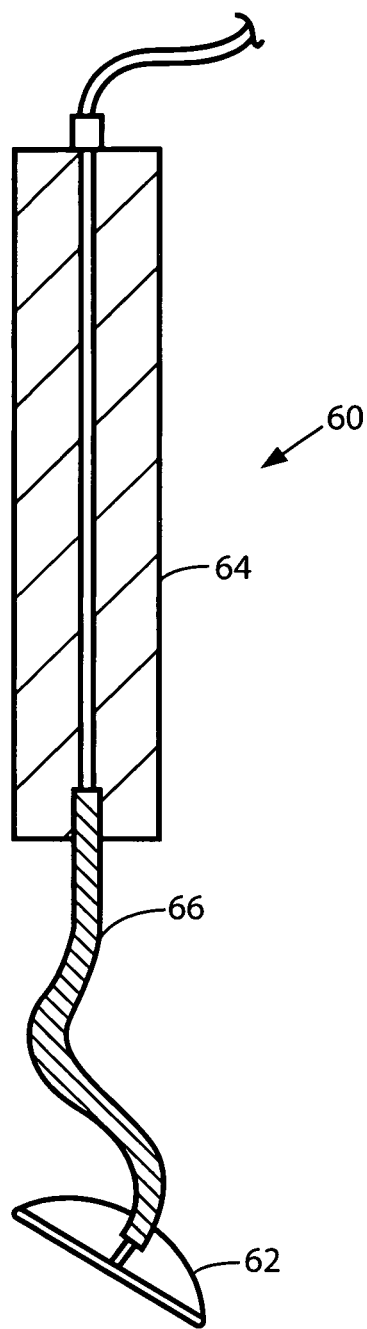
FIG. 4 is a cross-sectional view of a second exemplary embodiment of a paddle assembly.

Referring to FIG. 4 an alternate embodiment of the present invention paddle assembly 60 is shown. In this embodiment, a paddle head 62 and a paddle handle 64 are provided. The paddle head 62 and the paddle handle 64 are again coupled together by a flexible neck 66. However, the flexible neck 66 does not contain a spring and guide wires. Rather, the flexible neck 66 of the paddle assembly 60 is fabricated from a section of malleable metal. The malleable metal can be a tin alloy, brass alloy or the like that is rigid enough to hold form against gravity, yet malleable enough to be selectively bent into various configurations in the hands of a physician.

The malleable metal in the flexible neck 66 is preferably coated externally with a non-conductive coating 68, such as a dip plastic coating. In this manner, the electricity will not arc from the malleable metal into the surrounding tissue when the paddle assembly 60 is in use.

To use the paddle assembly 60, a physician would grip the paddle head 62 and the paddle handle 64 in opposite hands. The physician would then selectively bend the flexible neck 66 of the paddle assembly 60 until the paddle head 62 is in a desired orientation with respect to the paddle handle 64. The physician can then use the paddle assembly 60 in its unique orientation to touch the heart muscle.

It will be understood that the embodiments of the present invention are merely exemplary and that a person skilled in the art can make many modifications to the shown embodiment using functionally equivalent parts. For instance, in the embodiment of FIGS. 1-3, the structure of the flexible neck is provided by primarily using a metal spring. In an alternate embodiment, the spring can be replaced with an elastomeric element that would perform the same functions as the spring. Furthermore, the shape and size of the paddle head, neck section and paddle handle are a matter of design choice and can be configured to the whims of the manufacturer. All such variations, modifications and alternate embodiments are intended to be included within the scope of the present invention as set forth in the claims.

What is claimed is:

1. A defibrillator paddle assembly for use during open-heart surgery comprising:
a handle;
a paddle head having a conductive surface thereon; and a spring having a first end anchored to said handle and a second end anchored to said paddle head, therein coupling said handle to said paddle head, said spring being selectively bendable into nonlinear configurations between said first end and said second end into different shapes, wherein said spring enables said paddle head to move through a range of different orientations with respect to said handle; and an adjustment mechanism disposed on said handle for selectively bending said spring and moving said paddle head through said range of different orientations.

2. The assembly according to claim 1, wherein said spring is in a compressed state.

3. The assembly according to claim 2, further including guide wires that extend through said spring between said paddle head and said handle, wherein said guide wires maintain said spring in said compressed state.

4. The assembly according to claim 3, wherein said spring provides tautness to said guide wires and said assembly further includes an adjustment mechanism for selectively varying said tautness of said guide wires.

5. The assembly according to claim 3 further including a wobble plate disposed within said handle, wherein said guide wires attach to said wobble plate.

6. The assembly according to claim 5, further including a lever coupled to said wobble plate for manually manipulating said wobble plate.

7. A defibrillation system for use in shocking the heart during an open heart surgical procedure, said system comprising:

a control unit for controlling an electric charge between a first terminal and a second terminal;

a conductive pad coupled to said first terminal by a first wire; and a paddle assembly coupled to said second terminal by a second wire, said paddle assembly having a handle, a head, and a spring, wherein said spring has a first end coupled to said handle and an opposite second end coupled to said head, and wherein said spring is selectively deformable into nonlinear configurations between said first end and said second end, and an adjustment control on said handle for selectively bending said elongated neck.

8. A defibrillator paddle assembly for use during open-heart surgery comprising:

a handle;

a paddle head having a conductive surface thereon; and a spring having a first end anchored to said handle and a second end anchored to said paddle head, therein coupling said handle to said paddle head, said spring being in a compressed state and selectively bendable into nonlinear configurations between said first end and said second end into different shapes, wherein said spring enables said paddle head to move through a range of different orientations with respect to said handle; and guide wires that extend through said spring between said paddle head and said handle, wherein said guide wires maintain said spring in said compressed state.

* * * * *